(12) United States Patent
Graboi et al.

(10) Patent No.: US 8,374,666 B2
(45) Date of Patent: Feb. 12, 2013

(54) RETINOPATHY OF PREMATURITY DETERMINATION AND ALARM SYSTEM

(75) Inventors: Daniel G. Graboi, Encinitas, CA (US); Peter Doyle, Vista, CA (US)

(73) Assignee: Covidien LP, Mansfield, MA (US)

( * ) Notice: Subject to any disclaimer, the term of this patent is extended or adjusted under 35 U.S.C. 154(b) by 237 days.

(21) Appl. No.: 12/789,717

(22) Filed: May 28, 2010

(65) Prior Publication Data

US 2011/0295093 A1    Dec. 1, 2011

(51) Int. Cl.
*A61B 5/00* (2006.01)
(52) U.S. Cl. ........................................ 600/323
(58) Field of Classification Search ................ 600/323
See application file for complete search history.

(56) References Cited

U.S. PATENT DOCUMENTS

| | | | |
|---|---|---|---|
| 5,865,736 A | 2/1999 | Baker et al. | |
| 5,891,023 A | 4/1999 | Lynn | |
| 6,754,516 B2 | 6/2004 | Mannheimer | |
| 6,839,581 B1 | 1/2005 | El-Solh et al. | |
| 6,840,904 B2 | 1/2005 | Goldberg | |
| 6,930,608 B2 | 8/2005 | Grajales et al. | |
| 7,066,173 B2 | 6/2006 | Banner et al. | |
| 7,123,950 B2 | 10/2006 | Mannheimer | |
| 7,171,251 B2 | 1/2007 | Sarussi et al. | |
| 7,210,478 B2 | 5/2007 | Banner et al. | |
| 7,246,620 B2 | 7/2007 | Conroy | |
| 7,415,297 B2 | 8/2008 | Al-Ali | |
| 2003/0078480 A1* | 4/2003 | Claure et al. | 600/323 |
| 2003/0140924 A1 | 7/2003 | Aylsworth et al. | |
| 2005/0039742 A1 | 2/2005 | Hickle | |
| 2005/0065417 A1 | 3/2005 | Ali et al. | |
| 2005/0222502 A1 | 10/2005 | Cooper | |
| 2006/0042631 A1 | 3/2006 | Martin et al. | |
| 2006/0106649 A1 | 5/2006 | Eggers et al. | |
| 2006/0122867 A1 | 6/2006 | Eggers et al. | |
| 2006/0136271 A1 | 6/2006 | Eggers et al. | |
| 2006/0143051 A1 | 6/2006 | Eggers et al. | |

(Continued)

FOREIGN PATENT DOCUMENTS

| | | |
|---|---|---|
| JP | 23169791 | 6/2003 |
| WO | WO9309711 | 5/1993 |
| WO | WO0176461 | 10/2001 |
| WO | WO2004041073 | 5/2004 |
| WO | WO2006067725 | 6/2006 |
| WO | WO2008043864 | 4/2008 |

OTHER PUBLICATIONS

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

(Continued)

*Primary Examiner* — Rodney Fuller (57) ABSTRACT

Methods and system for determining a likelihood of possible retinopathy of prematurity and alerting a caregiver of such likelihood may employ oxygen saturation measurements. According to certain embodiments, an apparatus for determining a risk of retinopathy of prematurity in a patient may include a processing unit. The processing unit is configured to determine whether an oxygen saturation level of the patient extends beyond an oxygen saturation threshold, determine an extent that the oxygen saturation level of the patient extends beyond the oxygen saturation threshold, and trigger an alarm when the extent that the oxygen saturation level of the patient extends beyond the oxygen saturation threshold exceeds a threshold at which the patient may be at risk of developing retinopathy of prematurity. The apparatus may also include a display unit configured to present the alarm in response to the trigger from the processing unit.

20 Claims, 10 Drawing Sheets

U.S. PATENT DOCUMENTS

| | | |
|---|---|---|
| 2006/0150970 A1 | 7/2006 | Lampotang et al. |
| 2006/0185669 A1 | 8/2006 | Bassovitch |
| 2006/0190302 A1 | 8/2006 | Eggers et al. |
| 2006/0225737 A1 | 10/2006 | Iobbi |
| 2006/0235324 A1 | 10/2006 | Lynn |
| 2006/0241708 A1 | 10/2006 | Boute |
| 2006/0281983 A1* | 12/2006 | Al-Ali et al. ............... 600/323 |
| 2007/0027375 A1 | 2/2007 | Melker et al. |
| 2007/0032714 A1 | 2/2007 | Mannheimer |
| 2007/0077200 A1 | 4/2007 | Baker |
| 2007/0123785 A1 | 5/2007 | Lu et al. |
| 2007/0149871 A1 | 6/2007 | Sarussi et al. |
| 2007/0167694 A1 | 7/2007 | Causevic et al. |
| 2007/0203406 A1 | 8/2007 | Anderson et al. |
| 2008/0066752 A1 | 3/2008 | Baker et al. |
| 2008/0076962 A1 | 3/2008 | Miyagawa et al. |
| 2008/0076977 A1 | 3/2008 | Mannheimer et al. |
| 2008/0076988 A1 | 3/2008 | Sarussi et al. |
| 2008/0076990 A1 | 3/2008 | Sarussi et al. |
| 2008/0076992 A1 | 3/2008 | Hete et al. |
| 2008/0077022 A1 | 3/2008 | Baker |
| 2008/0091088 A1 | 4/2008 | Kiani |
| 2008/0097175 A1 | 4/2008 | Boyce et al. |
| 2008/0183058 A1 | 7/2008 | Mannheimer |
| 2008/0228052 A1 | 9/2008 | Al-Ali |
| 2008/0300471 A1 | 12/2008 | Al-Ali et al. |
| 2008/0314385 A1 | 12/2008 | Brunner et al. |
| 2009/0171167 A1* | 7/2009 | Baker, Jr. ............... 600/301 |
| 2009/0241958 A1* | 10/2009 | Baker, Jr. ............... 128/204.23 |
| 2011/0295094 A1* | 12/2011 | Doyle et al. ............... 600/340 |

OTHER PUBLICATIONS

Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

East, Christine E., et al.; "Fetal Oxygen Saturation and Uterine Contractions During Labor," *American Journal of Perinatology*, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society*, vol. 20, No. 6, p. 3072-3075, 1998.

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Kaestle, S.; "Determining Artefact Sensitivity of New Pulse Oximeters in Laboratory Using Signals Obtained from Patient," *Biomedizinische Technik*, vol. 45 (2000).

Cysewska-Sobusaik, Anna; "Metrological Problems With noninvasive Transillumination of Living Tissues," *Proceedings of SPIE*, vol. 4515, pp. 15-24 (2001).

Belal, Suliman Yousef, et al.; "A fuzzy system for detecting distorted plethysmogram pulses in neonates and paediatric patients," *Physiol. Meas.*, vol. 22, pp. 397-412 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Chan, K.W., et al.; "17.3: Adaptive Reduction of Motion Artifact from Photoplethysmographic Recordings using a Variable Step-Size LMS Filter," *IEEE*, pp. 1343-1346 (2002).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Yoon, Gilwon, et al.; Multiple diagnosis based on Photoplethysmography: hematocrit, SpO2, pulse and respiration, *Optics in Health Care and Biomedical optics: Diagnostics and Treatment; Proceedings of the SPIE*, vol. 4916; pp. 185-188 (2002).

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Johansson, A.; "Neural network for photoplethysmographic respiratory rate monitoring," *Medical & Biological Engineering & Computing*, vol. 41, pp. 242-248 (2003).

U.S. Appl. No. 12/789,718, filed May 28, 2010, Doyle et al.

Odagiri, Y.; "Pulse Wave Measuring Device," Micromechatronics, vol. 42, No. 3, pp. 6-11 (Sep. 1998) (Article in Japanese —contains English summary of article).

Plastic Logic; http://www.plasticlogic.com/product.html; 2000.

Hamilton, Patrick S., et al.; "Effect of Adaptive Motion-Artifact Reduction on QRS Detection," Biomedical Instrumentation & Technology, pp. 197-202 (May/Jun. 2000).

Kim, J.M., et al.; "Signal Processing Using Fourier & Wavelet Transform," pp. II-310 —II-311 (Jul. 15-19, 2001).

Huang, J., et al.; "Low Power Motion Tolerant Pulse Oximetry," Abstracts, A7, p. S103. (Mar. 8-9, 2002).

Neumann, R., et al.; "Fourier Artifact suppression Technology Provides Reliable SpO2," Abstracts, A11, p. S105. (Mar. 8-9, 2002).

Spigulis, Janis, et al.; "Optical multi-channel sensing of skin blood pulsations," Optical Sensing, Proceedings of SPIE, vol. 5459, pp. 46-53 (2004).

Addison, Paul S., et al.; "A novel time-frequency-based 3D Lissajous figure method and its application to the determination of oxygen saturation from the photoplethysmogram," Institute of Physic Publishing, Meas. Sci. Technol., vol. 15, pp. L15-L18 (2004).

Johnston, W.S., et al.; "Extracting Breathing Rate Infromation from a Wearable Reflectance Pulse Oximeter Sensor," Proceedings of the 26th Annual International conference of the IEEE EMBS, San Francisco, California; Sep. 1-5, 2004; pp. 5388-5391.

Active Matrix ePaper Displays; Innovating Display Solutions; SiPix; 2005.

First-Generation Electronic Paper Display from Phlips, Sony and E Ink to be Used in New Electronic Reading Devices; E Ink Corporation; 2005.

Electronic Paper Displays; E Ink Corporation; 2005.

Segmented ePaper Displays; Innovating Display Solutions; SiPix; 2005.

Kaufman, D, Davis M, Gurka M, Walsh B: Percentage of Time of Hypoxia and Hyperoxia and Retinopathy of Prematurity in VLBWs. E-PAS2009:2837.328, May 2, 2009.

\* cited by examiner

RETINOPATHY OF PREMATURITY DETERMINATION AND ALARM SYSTEM

BACKGROUND

The present disclosure relates generally to patient monitoring devices and, more particularly, to techniques for determining a likelihood of possible retinopathy of prematurity and alerting a caregiver of such likelihood.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of healthcare, caregivers (e.g., doctors and other healthcare professionals) often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

One technique for monitoring physiological characteristics of a patient is commonly referred to as pulse oximetry, and the devices built based upon pulse oximetry techniques are commonly referred to as pulse oximeters. Pulse oximeters may be used to measure and monitor various blood flow characteristics of a patient. For example, a pulse oximeter may be utilized to monitor the blood oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time-varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. A photo-plethysomograhpic waveform, which corresponds to the cyclic attenuation of optical energy through the patient's tissue, may be generated from the detected light. Additionally, one or more of the above physiological characteristics may be calculated based upon the amount of light absorbed or scattered. More specifically, the light passed through the tissue may be selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

In addition to monitoring a patient's physiological characteristics, a pulse oximeter or other patient monitor may alert a caregiver when certain physiological conditions are recognized. For example, a normal range for a particular physiological parameter of a patient may be defined by setting low and/or high threshold values for the physiological parameter, and an alarm may be generated by the patient monitor when a detected value of the physiological parameter is outside the normal range.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Normally in healthcare settings, the oxygen saturation levels of pediatric and adult patients are monitored to avoid or to minimize insufficient oxygenation of the arterial blood, often referred to as hypoxemia. However, in some settings it may be beneficial to also monitor for and minimize excessive oxygenation of the blood, often referred to as hyperoxemia. For example, in neonatal intensive care units (NICU), it may be desirable to monitor for hypoxemia and/or hyperoxemia to prevent retinopathy of prematurity (ROP), which is a disorder of the blood vessels of the retina that is common in premature infants. Hyperoxemia or hypoxemia ($SpO_2$ levels outside 88 percent to 92 percent) may correlate with the development of ROP in low birthweight or premature infants. Additionally, the cumulative duration of multiple hyperoxemic and hypoxemic events, as well as the severity of the events, may correlate with the development of ROP in these infants. Accordingly, an alarm system may be employed to monitor hypoxemia and/or hyperoxemia to provide an indication of a risk of developing ROP. Also, the alarm system may take into account specific factors relevant to the possible development of ROP, such as patient specific parameters including gestational age or weight, in order to set threshold values for the alarm system and to provide an indication or alarm to a caregiver that the patient may be at risk of developing ROP.

Figure 1:
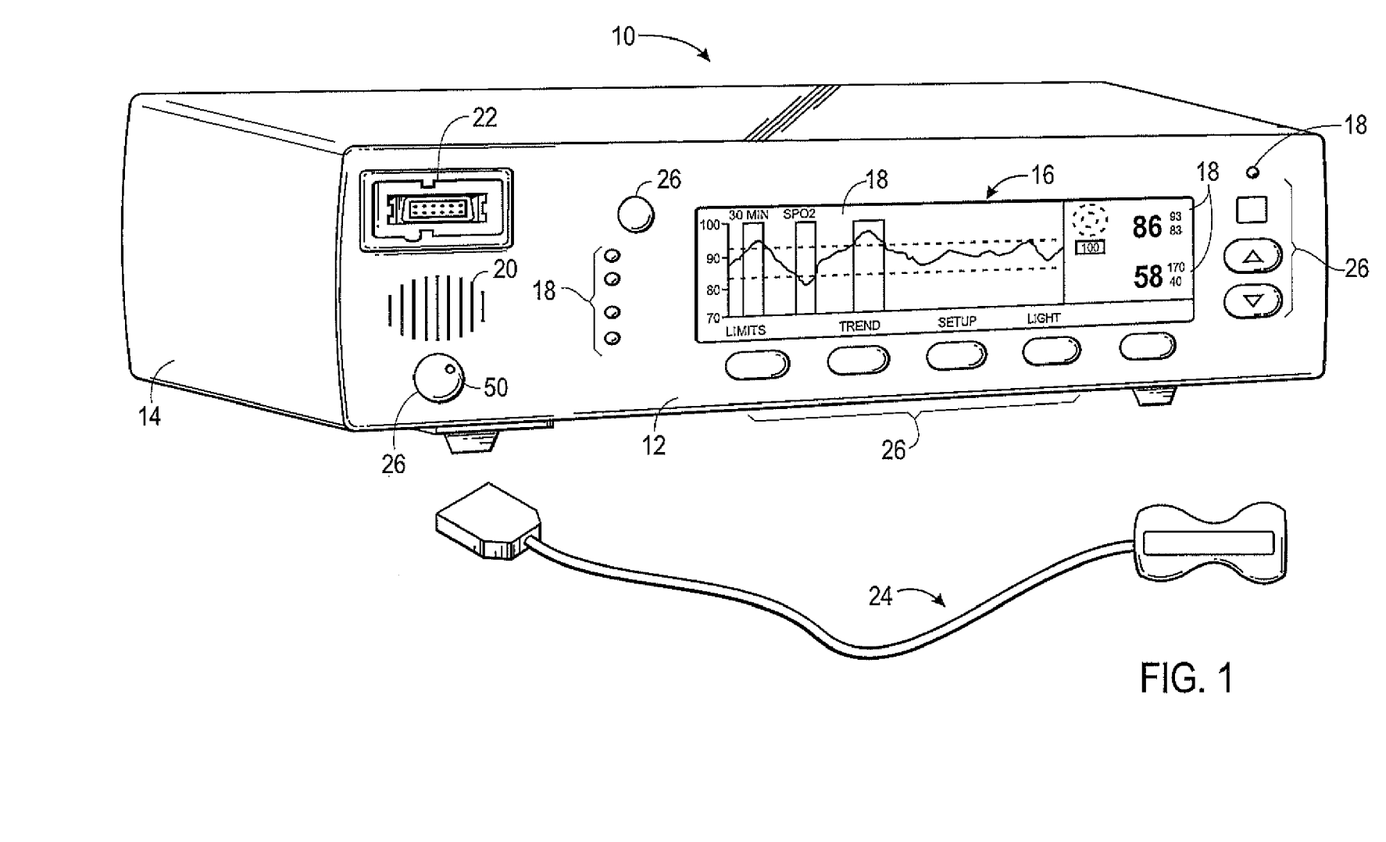
FIG. 1 a perspective view of a patient monitor in accordance with an embodiment.

FIG. 1 is a perspective view of an example of a patient monitor 10 in accordance with an embodiment of the present disclosure. For example, the patient monitor 10 may be a pulse oximeter, such as those available from Nellcor Puritan Bennett LLC of Boulder, Colo. As illustrated, the patient monitor 10 is a pulse oximeter that is configured to detect and monitor blood oxygen saturation levels, pulse rate, and so forth. It should be noted that while the illustrated embodiment includes a pulse oximeter, other embodiments may include different types of patient monitors 10. For example, the patient monitor 10 may be representative of a vital signs monitor, a critical care monitor, an obstetrical care monitor, or the like.

The illustrated patient monitor 10 includes a front panel 12 coupled to a body 14 of the monitor 10. The front panel 12 includes a display screen 16 and various indicators 18 (e.g., indicator lights and display screen graphics) that facilitate operation of the monitor 10 and observation of a patient's physiological metrics (e.g., pulse rate). Some of the indicators 18 are specifically provided to facilitate monitoring of a patient's physiological parameters. For example, the indicators 18 may include representations of the most recently measured values for $SpO_2$, pulse rate, index values, and/or pulse amplitude. In some embodiments, the indicators 18 may include an ROP indicator that provides an indication related to low and/or high oxygen saturation. For example, the ROP indicator 18 may be an annular indicator related to the duration and extent of low and/or high oxygen saturation events. Other indicators 18 may be specifically provided to facilitate operation of the monitor 10. For example, the indicators 18 may include an A/C power indicator, a low battery indicator, an alarm silence indicator, a mode indicator, and so forth. The front panel 12 may also include a speaker 20 for emitting audible indications (e.g., alarms), a sensor port 22 for coupling with a sensor 24 (e.g., a temperature sensor, a pulse oximeter sensor) and other monitor features.

Additionally, the front panel 12 may include various activation mechanisms 26 (e.g., buttons and switches) to facilitate management and operation of the monitor 10. For example, the front panel 12 may include function keys (e.g., keys with varying functions), a power switch, adjustment buttons, an alarm silence button, and so forth. It should be noted that in other embodiments, the indicators 18 and activation mechanisms 26 may be arranged on different parts of the monitor 10. In other words, the indicators 18 and activation mechanisms 26 need not be located on the front panel 12. Indeed, in some embodiments, activation mechanisms 26 are virtual representations in a display or actual components disposed on separate devices.

Figure 2:
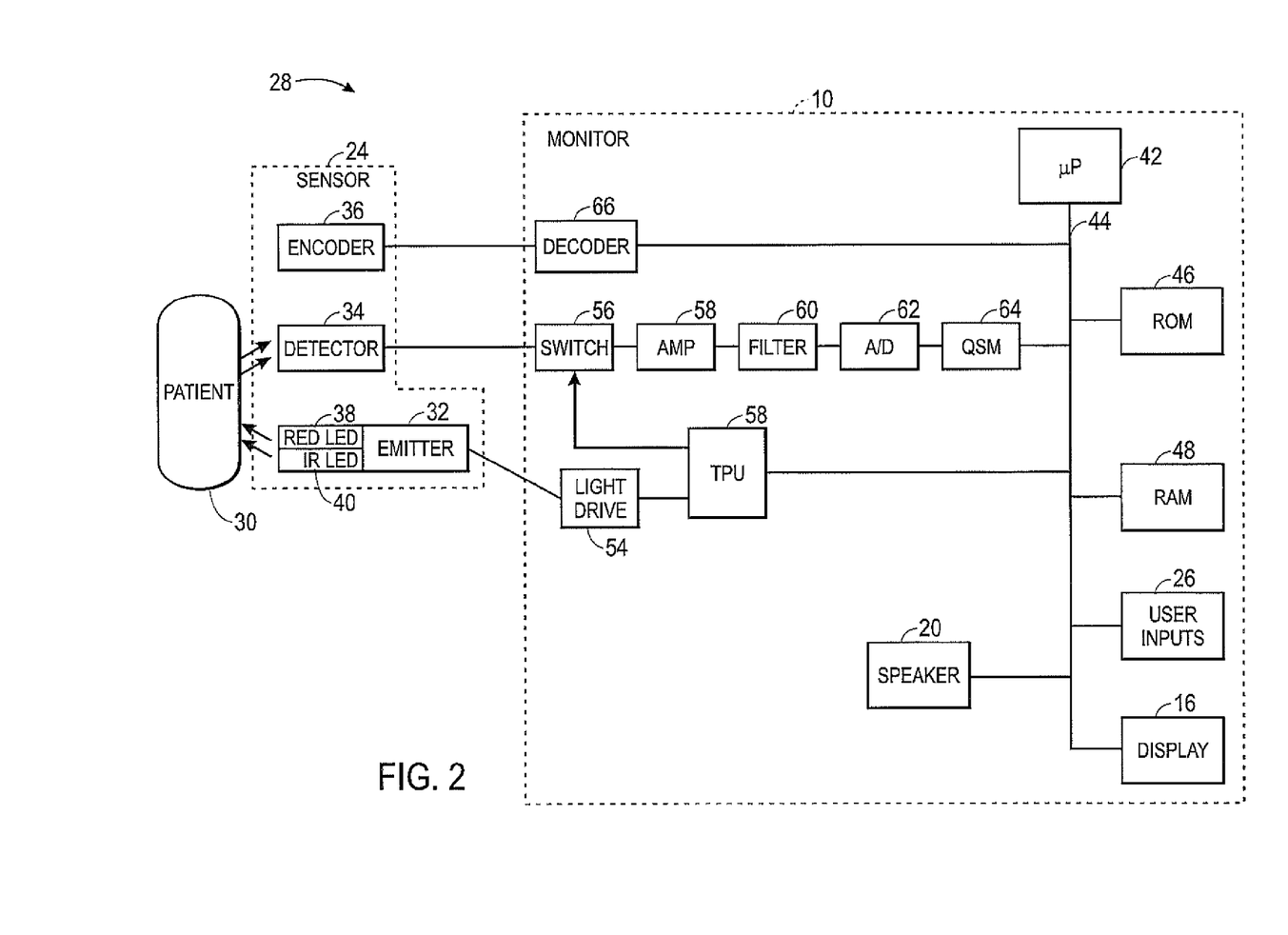
FIG. 2 is a simplified block diagram of an embodiment of a patient monitoring system in accordance with an embodiment.

Turning to FIG. 2, a simplified block diagram of a patient monitoring system 28 coupled to a patient 30 is illustrated in accordance with an embodiment. Specifically, certain components of the sensor 24 and the monitor 10 are illustrated in FIG. 2. The sensor 24 may include an emitter 32, a detector 34, and an encoder 36. It should be noted that the emitter 32 may be configured to emit at least two wavelengths of light, e.g., RED and IR, into a patient's tissue 30. Hence, the emitter 32 may include a RED LED 38 and an IR LED 40 for emitting light into the patient's tissue 30 at the wavelengths used to calculate the patient's physiological parameters. In certain embodiments, the RED wavelength may be between about 600 nm and about 700 nm, and the IR wavelength may be between about 800 nm and about 1000 nm. Alternative light sources may be used in other embodiments. For example, a single wide-spectrum light source may be used, and the detector 34 may be configured to detect light only at certain wavelengths. In another example, the detector 34 may detect a wide spectrum of wavelengths of light, and the monitor 10 may process only those wavelengths which are of interest. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present techniques.

In one embodiment, the detector 34 may be configured to detect the intensity of light at the RED and IR wavelengths. In operation, light enters the detector 34 after passing through the patient's tissue 30. The detector 34 may convert the intensity of the received light into an electrical signal. The light intensity may be directly related to the absorbance and/or reflectance of light in the tissue 30. That is, when more light at a certain wavelength is absorbed or reflected, less light of that wavelength is typically received from the tissue by the detector 34. After converting the received light to an electrical signal, the detector 34 may send the signal to the monitor 10, where physiological parameters may be calculated based on the absorption of the RED and IR wavelengths in the patient's tissue 30.

The encoder 36 may contain information about the sensor 24, such as what type of sensor it is (e.g., whether the sensor is intended for placement on a forehead or digit) and the wavelengths of light emitted by the emitter 32. This information may allow the monitor 10 to select appropriate algorithms and/or calibration coefficients for calculating the patient's physiological parameters. The encoder 36 may, for instance, be a coded resistor whose value corresponds to the type of the sensor 10 and/or the wavelengths of light emitted by the emitter 32. These coded values may be communicated to the monitor 10, which determines how to calculate the patient's physiological parameters. In another embodiment, the encoder 32 may be a memory on which one or more of the following information may be stored for communication to the monitor 10: the type of the sensor 24; the wavelengths of light emitted by the emitter 34; the proper calibration coefficients and/or algorithms to be used for calculating the patient's physiological parameters; the proper threshold levels based on inputted patient parameters and other factors to be used in monitoring an alarm for the risk of developing ROP; and algorithms to be used for determining the risk of developing ROP based on the patient's calculated physiological parameters and inputted patient parameters such as gestational age and weight, and other factors such as duration of hyperoxemic and hypoxemic events over a given period of time. Examples of pulse oximetry sensors configured to cooperate with pulse oximetry monitors may include OxiMax® sensors available from Nellcor Puritan Bennett LLC.

Signals from the detector 34 and the encoder 36 may be transmitted to the monitor 10. The monitor 10 generally may include one or more processors 42 connected to an internal bus 44. Also connected to the bus may be a read-only memory (ROM) 46, a random access memory (RAM) 48, user inputs 26, the display 16, or the speaker 20. A time processing unit (TPU) 52 may provide timing control signals to a light drive circuitry 54 which controls when the emitter 32 is illuminated and the multiplexed timing for the RED LED 38 and the IR LED 40. The TPU 52 controls the gating-in of signals from detector 34 through a switching circuit 56. These signals may be sampled at the proper time, depending upon which light source is illuminated. The received signal from the detector 34 may be passed through an amplifier 58, a low pass filter 60, and an analog-to-digital converter 62. The digital data may then be stored in a queued serial module (QSM) 64 for later downloading to the RAM 48 as the QSM 64 fills up. In one embodiment, there may be multiple separate parallel paths having the amplifier 58, the filter 60, and the A/D converter 62 for multiple light wavelengths or spectra received.

The monitor 10 may be provided information from multiple sources either to determine the patient's physiological parameters or the threshold levels for an alarm to be used in monitoring the patient 30 for the risk of developing ROP. The processor(s) 42 of the monitor 10 may determine the patient's physiological parameters, such as $SpO_2$ and pulse rate, using various algorithms and/or look-up tables based on information received from the sensor 24. For example, signals corresponding to information about the sensor 24 (e.g., sensor type) may be transmitted from the encoder 36 to a decoder 66. The decoder 66 may translate these signals to enable the processor(s) 42 to determine the proper method for calculating the patient's physiological parameters, for example, based on algorithms or look-up tables stored in the ROM 46.

Also, the processor(s) 42 of the monitor 10 may determine the threshold levels for an alarm that monitors the risk of developing ROP using various algorithms and/or look-up tables. These algorithms and/or look-up tables allow the processor(s) 42 to determine the proper threshold values based on inputted patient parameters, such as gestational age or weight, for measured physiological parameters (e.g., $SpO_2$). The encoder 36 may contain the algorithms and/or look-up tables to determine the various threshold values corresponding to the inputted patient parameters and may transmit this information to a decoder 66. The decoder 66 may translate this information to the processor(s) 42 to determine the threshold levels based on the inputted patient parameters. Alternatively, the algorithms and/or look-up tables to determine the thresholds may be stored in the ROM 46.

As mentioned above, inputted patient parameters may be used to determine the thresholds for an alarm to monitor for the risk of developing ROP. Patient parameters may be input by the caregiver using the user inputs 26 located on the monitor 10, in conjunction with options and menus that may be provided on the display screen 16 of the monitor 10. The user inputs 26 may also be used to change the thresholds for measured physiological parameters on the monitor 10. For example, the display 16 may exhibit minimum and/or maximum $SpO_2$ thresholds and a selection of ROP integral threshold values, which the caregiver may change using the user inputs 26.

The patient monitoring system 28 illustrated in FIG. 2 may be employed to monitor hyperoxemic and/or hypoxemic events to provide an indication of the risk of developing ROP. Generally speaking, an ROP alarm system for hypoxemic events may operate by integrating an area between a threshold and a patient's measured physiological parameters over time, as in a graph 76 illustrated in FIG. 3. The patient's $SpO_2$ readings may be displayed as a plot 78 in the graph 76. Similarly, a lower threshold $SpO_2$ value (e.g., 88 percent) may be displayed as a line 80 in the graph 76. As the patient's measured $SpO_2$ (plot 78) drops below the lower threshold value (line 80), the ROP system measures an area 82 (shaded in FIG. 3) by integrating the difference between the plot 78 and the line 80 when the plot 78 is below the line 80. The area 82 may be known as the ROP integral value, and it is a measure of saturation (percent deviation below the lower $SpO_2$ threshold value) versus time (minutes). When the total ROP integral value exceeds a ROP integral threshold value (e.g., a preset integral value based on patient specific parameters, as well as other factors, or a user-input integral value), the caregiver may be alerted that the patient may be at risk for developing ROP. A significant desaturation event 84 (e.g., a large drop in $SpO_2$) may cause the alarm to activate relatively quickly because the ROP integral threshold value may be exceeded in a relatively short period of time 86. In contrast, a minor desaturation event 88 (e.g., a drop in $SpO_2$ (plot 78) to just below the lower threshold (line 80)) may not cause the alarm to be activated for a relatively long time, e.g., 80 minutes. That is, the minor desaturation event 88 may continue for a relatively long period of time 90 before the ROP integral threshold value is exceeded. ROP integral threshold values may range up to 240 minutes. Similar to the ROP integral value, the ROP integral threshold value may be a measure of saturation (percent deviation below the lower $SpO_2$ threshold value) over time (minutes).

Figure 3:
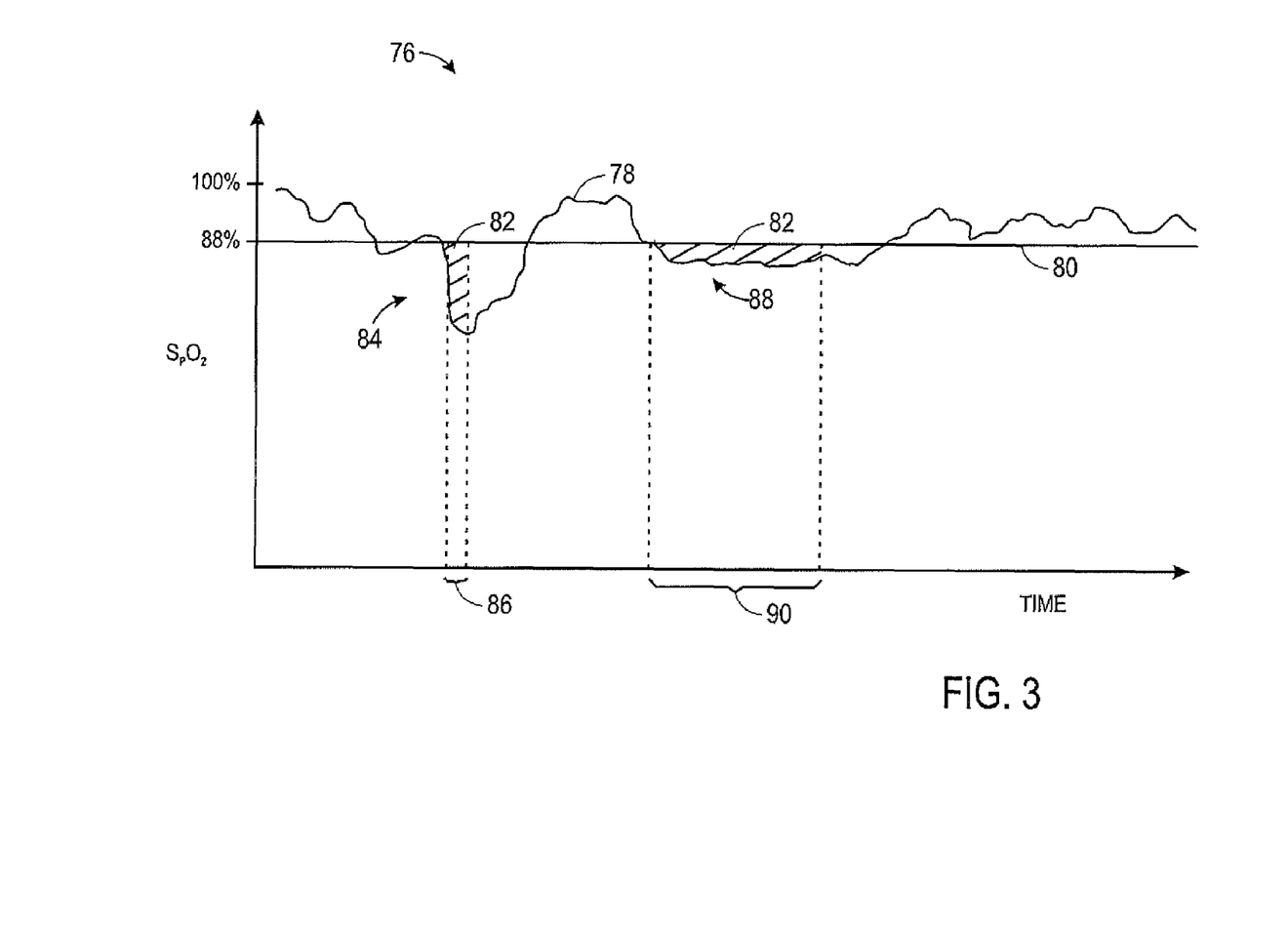
FIG. 3 is a graph illustrating a patient's measured $SpO_2$ versus time in accordance with one embodiment.
Figure 4:
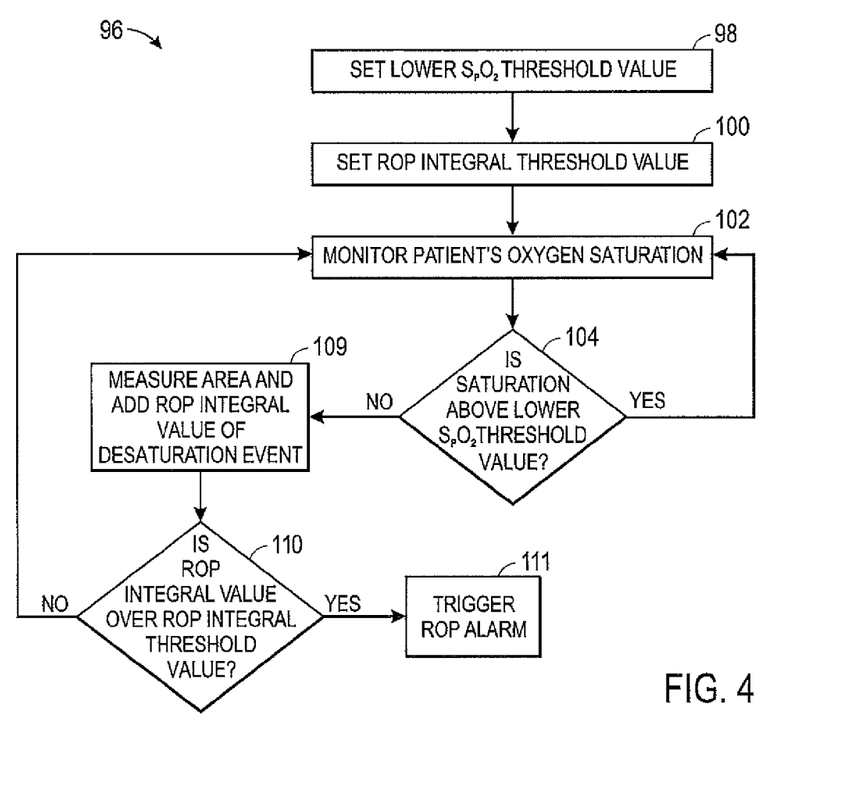
FIG. 4 is a flow chart illustrating the operation of a retinopathy of prematurity alarm in accordance with the embodiment of FIG. 3.

The manner in which the ROP alarm system for hypoxemic events, as described with respect to FIG. 3, operates may be better understood with reference to the flow chart 96 presented in FIG. 4. The monitor 10 may include an ROP module that may be activated to monitor the risk of developing ROP. Once activated, a lower $SpO_2$ threshold value for oxygen saturation may be set (block 98), as well as an ROP integral threshold value (block 100). The caregiver may set the lower $SpO_2$ threshold value and ROP integral threshold value. Alternatively, the caregiver may desire the monitor 10 to automatically set the lower threshold value, particularly in specific patient populations such as premature infants. For example, the monitor 10 may be able to take into account patient specific features such as gestational age or weight, as well as other factors, to obtain the appropriate threshold value for the patient 30, as described in more detail below. The monitor 10 may monitor the patient's oxygen saturation (block 102), and the saturation level may be compared to the lower threshold value to determine if the saturation level is above the lower $SpO_2$ threshold value (block 104). If the saturation level is above the lower threshold value, then monitoring of the patient's oxygen saturation may continue (block 102).

If the saturation level is not above the lower $SpO_2$ threshold value, i.e., a low saturation or desaturation event occurs where the saturation level deviates below the lower threshold value, then an area or ROP integral value may be measured as a product of the duration of the desaturation event and the amount or percentage points the saturation level deviates below the lower threshold value and added to the total ROP integral value (block 109). For example, if the lower threshold value is set at 88 percent, then a saturation value of 86 percent would deviate from the lower threshold value by 2 points. These points may then be multiplied by the time or duration of an event (e.g., 1 minute) to get an area or ROP value of 2. As mentioned above, the ROP integral threshold value, ranging up to 240 minutes, may be preset or entered by a caregiver. Upon the addition of the ROP integral value, a determination may be made as to whether the total ROP integral value is over the ROP integral threshold value (block 110). If the total ROP integral value does not exceed the ROP integral threshold value, then monitoring of the patient's oxygen saturation may continue (block 102).

If during the monitoring of a patient's oxygen saturation levels, the total ROP integral value meets the ROP integral threshold value an ROP alarm may be triggered (block 111). The ROP alarm may alert the caregiver that the patient 30, e.g., the premature infant, has suffered enough hypoxemic events that pose a risk of developing ROP. The caregiver may want to be aware of such a risk to begin a therapy or treatment or to alter an existing therapy or treatment to the patient 30 to avoid an increased risk of developing ROP or to alleviate any damage that may have already occurred. The alarm may take the form of a visual alarm on the monitor 10, an audible alarm through the speaker 20 of the monitor 10, and/or a combination thereof. Also, the alarm may be remotely located from the monitor 10. The visual alarm may be displayed on the display screen 16 of the monitor 10 or may be given via one of the indicators 18 located on the monitor 10. The alarm may be associated with a color (e.g., red) to get the attention of the caregiver that the patient 30 is in need of medical attention. The alarm may also flash.

While the monitoring of hypoxemic events to determine a likelihood of ROP has been discussed above, some embodiments of ROP alarm systems may be employed to monitor hyperoxemic events. An ROP alarm system for hyperoxemic events may operate by integrating an area between a threshold and a patient's measured physiological parameters over time, as in a graph 112 illustrated in FIG. 5. The patient's $SpO_2$ readings may be displayed as a plot 114 in the graph 112. Similarly, an upper threshold $SpO_2$ value (e.g., 92 percent) may be displayed as a line 116 in the graph 112. As the patient's measured $SpO_2$ (plot 114) rises above the upper threshold value (line 116), the ROP system measures an area 118 (shaded in FIG. 5) by integrating the difference between the plot 114 and the line 116 when the plot 114 is above the line 116. The area 118 may be known as the ROP integral value, and it is a measure of saturation (percent deviation above the upper $SpO_2$ threshold value) versus time (minutes). When the total ROP integral value exceeds a ROP integral threshold value (e.g., a preset integral value based on patient specific parameters, as well as other factors, or a user-input integral value), the caregiver may be alerted that the patient may be at risk for developing ROP. A significant high saturation event 120 (e.g., a large increase in $SpO_2$) may cause the alarm to activate relatively quickly because the ROP integral threshold value may be exceeded in a relatively short period of time 122. In contrast, a minor high saturation event 124 (e.g., an increase in $SpO_2$ (plot 114) to just above the upper threshold (line 116)) may not cause the alarm to be activated for a relatively long time, e.g., 80 minutes. That is, the minor high saturation event 124 may continue for a relatively long period of time 126 before the ROP integral threshold value is exceeded. ROP integral threshold values may range up to 240 minutes.

Figure 5:
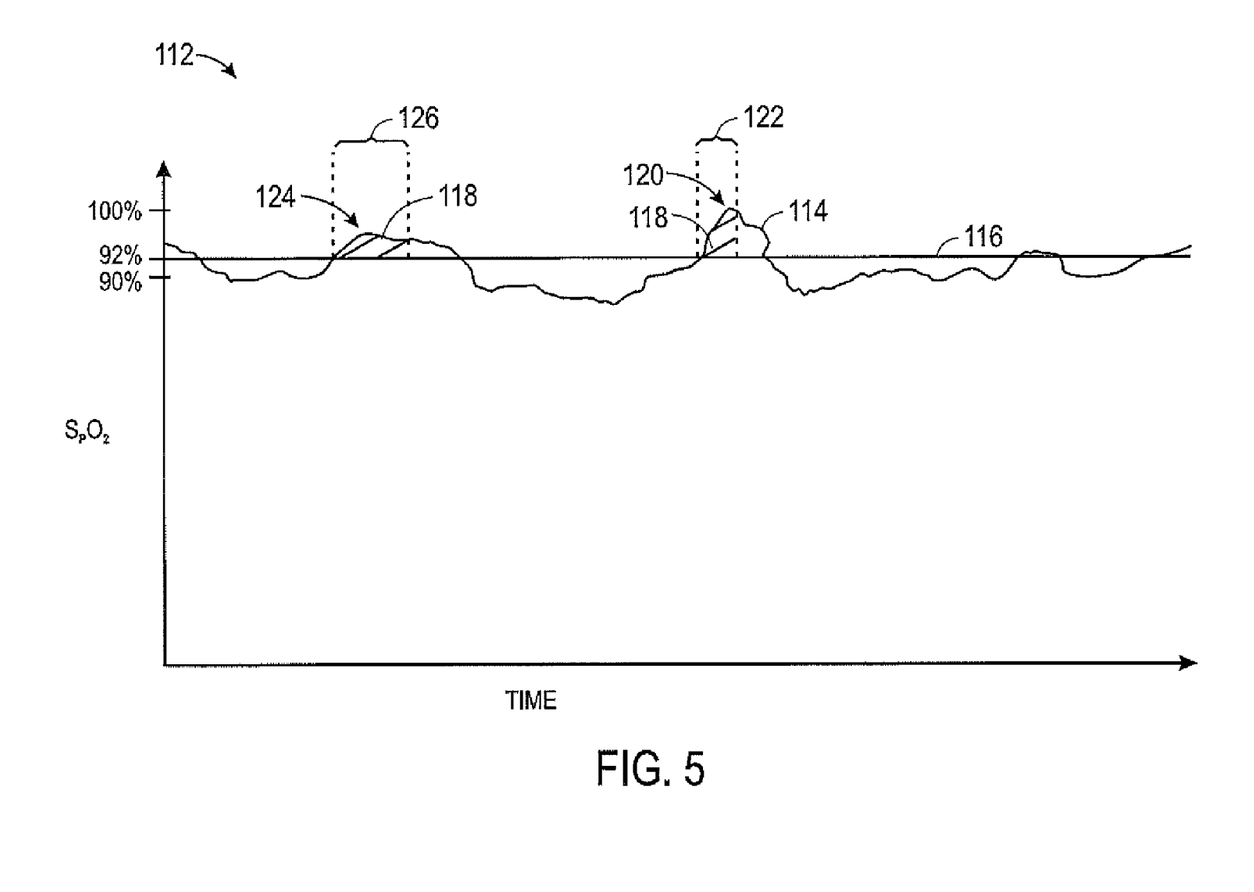
FIG. 5 is another graph illustrating a patient's measured $SpO_2$ versus time in accordance with another embodiment.
Figure 6:
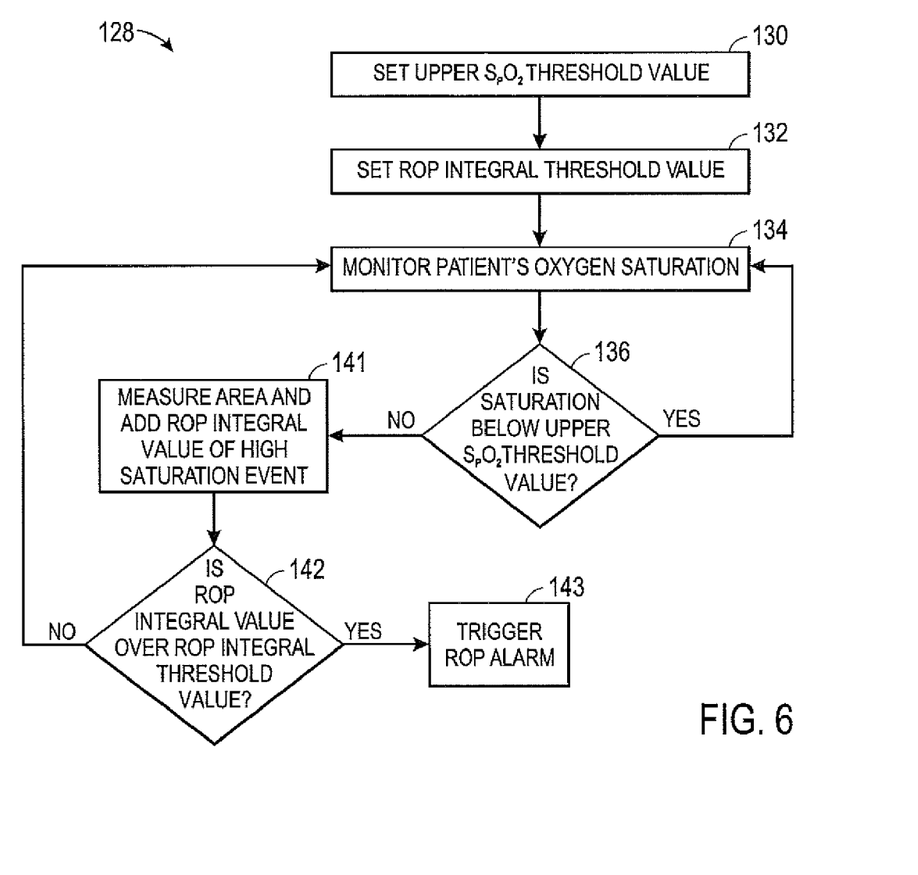
FIG. 6 is a another flow chart illustrating the operation of an retinopathy of prematurity alarm in accordance with the embodiment of FIG. 5.

The manner in which the ROP alarm system for hyperoxemic events as described with respect to FIG. 5 operates may be better understood with reference to the flow chart 128 presented in FIG. 6. As mentioned above, the monitor 10 may include an ROP module that may be activated to monitor the risk of developing ROP. Similar to method 96 above, once activated, an upper $SpO_2$ threshold value for oxygen saturation may be set (block 130), as well as an ROP integral threshold value (block 132). The caregiver may set the upper $SpO_2$ threshold value and ROP integral threshold value. Alternatively, the caregiver may desire the monitor 10 to automatically set the upper threshold value, particularly in specific patient populations such as premature infants. As mentioned above, the monitor 10 may be able to select the appropriate threshold value based on specific patient features. The monitor 10 may monitor the patient's oxygen saturation (block 134), and the saturation level may be compared to the upper $SpO_2$ threshold value to determine if the saturation level is below the upper $SpO_2$ threshold value (block 136). If the saturation level is above the lower threshold value, then monitoring of the patient's oxygen saturation may continue (block 134).

If the saturation level is not below the upper $SpO_2$ threshold value, i.e., a high saturation event occurs where the saturation level deviates above the upper threshold value, then an area or ROP integral value may be measured as a product of the duration of the high saturation event and the amount or percentage points the saturation level deviates above the upper threshold value and added to the total ROP integral value (block 141). For example, if the upper threshold value is set at 92 percent, then a saturation value of 95 percent would deviate from the upper threshold value by 3 points. These points may then be multiplied by the time or duration of an event (e.g., 2 minutes) to get an area or ROP integral value of 6. As mentioned above, the ROP integral threshold value, ranging up to 240 minutes, may be preset or entered by a caregiver. Upon the addition of the ROP integral value, a determination may be made as to whether the total ROP integral value is over the ROP integral threshold value (block 142). If the total ROP integral value does not exceed the ROP integral threshold value, then monitoring of the patient's oxygen saturation may continue (block 134).

If during the monitoring of a patient's oxygen saturation levels, the total ROP integral value meets the ROP integral threshold value an ROP alarm may be triggered (block 143). The ROP alarm may alert the caregiver that the patient 30, e.g., the premature infant, has suffered enough hyperoxemic events that pose a risk of developing ROP. The caregiver may want to be aware of such a risk to begin a therapy or treatment or to alter an existing therapy or treatment to the patient 30 to avoid an increased risk of developing ROP or to alleviate any damage that may have already occurred. The alarm may be as described above.

While the monitoring of either hypoxemic or hyperoxemic events to determine a likelihood of ROP has been discussed above, some embodiments of ROP alarm systems may be employed to monitor both hypoxemic and hyperoxemic events. The cumulative experience of repeated hypoxemic and hyperoxemic events may correlate with the development of ROP, as well as other conditions, in premature infants. Similar to the embodiments above, the ROP alarm system for both hypoxemic and hyperoxemic events may operate by integrating an area between a threshold and a patient's measured physiological parameters over time, as in a graph 144 illustrated in FIG. 7. The patient's $SpO_2$ readings may be displayed as a plot 146 in the graph 144. Similarly, an upper threshold $SpO_2$ value (e.g., 93 percent) and a lower threshold $SpO_2$ value (e.g., 83 percent) may be displayed as lines 148 and 150, respectively, in the graph 144. In some embodiments, only a single threshold $SpO_2$ value may be displayed. As the patient's measured $SpO_2$ (plot 146) rises above the upper threshold value (line 148) or drops below the lower threshold value (line 150), the ROP system measures an area 152 (shaded in FIG. 7) by integrating the difference between the plot 146 and the line 148 when the plot 146 is above the line 148 or the difference between the plot 146 and the line 150 when the plot 146 is below the line 150. In some embodiments, only a single threshold $SpO_2$ value may be displayed and deviations above and below the single threshold value integrated. The area 152 may be known as the ROP integral value, and it is a measure of saturation (percent deviation above upper $SpO_2$ threshold value or below lower $SpO_2$ threshold value) versus time (minutes). When the total ROP integral value exceeds an ROP integral threshold value (e.g., a preset integral value, as well as other factors, based on patient specific parameters or a user-input integral value), the caregiver may be alerted that the patient may be at risk for developing ROP. A significant high saturation event 154 (e.g., a large increase in $SpO_2$) or significant desaturation event 156 (e.g., a large decrease in $SpO_2$) may cause the alarm to activate relatively quickly because the ROP integral threshold value may be exceeded in a relatively short period of time 158 (for event 154) or 160 (for event 156). In contrast, a minor high saturation event 162 (e.g., an increase in $SpO_2$ (plot 146) to just above the upper threshold (line 148)) or a minor desaturation event 164 (e.g., a decrease in $SpO_2$ (plot 146) to just below the lower threshold (line 150)) may not cause the alarm to be activated for a relatively long time, e.g., 80 minutes. That is, the minor high saturation event 162 or minor desaturation event 164 may continue for a relatively long period of time 166 (for event 162) or 168 (for event 164) before the ROP integral threshold value is exceeded. ROP integral threshold values may range up to 240 minutes.

Figure 7:
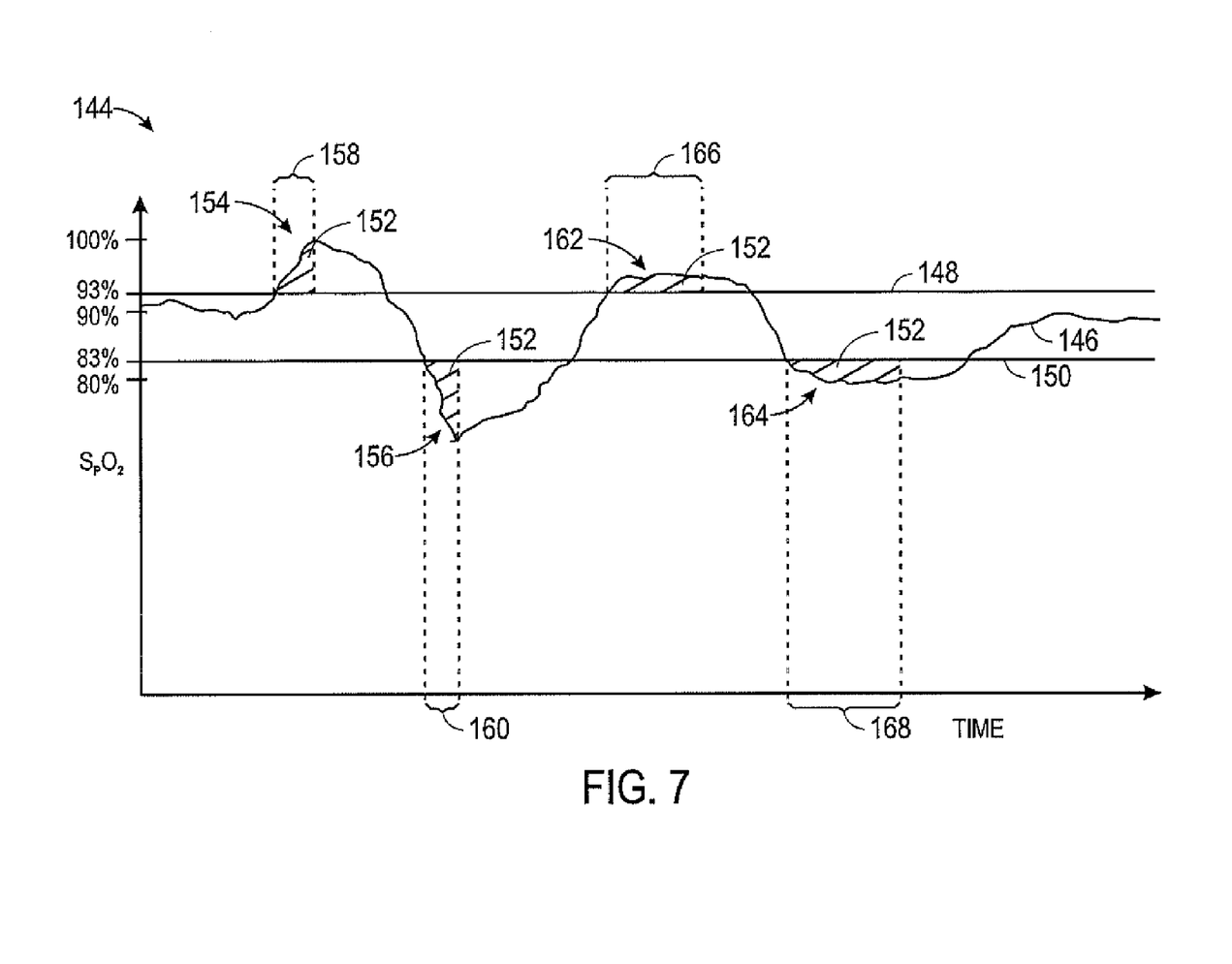
FIG. 7 is a further graph illustrating a patient's measured $SpO_2$ versus time in accordance with yet another embodiment.
Figure 8:
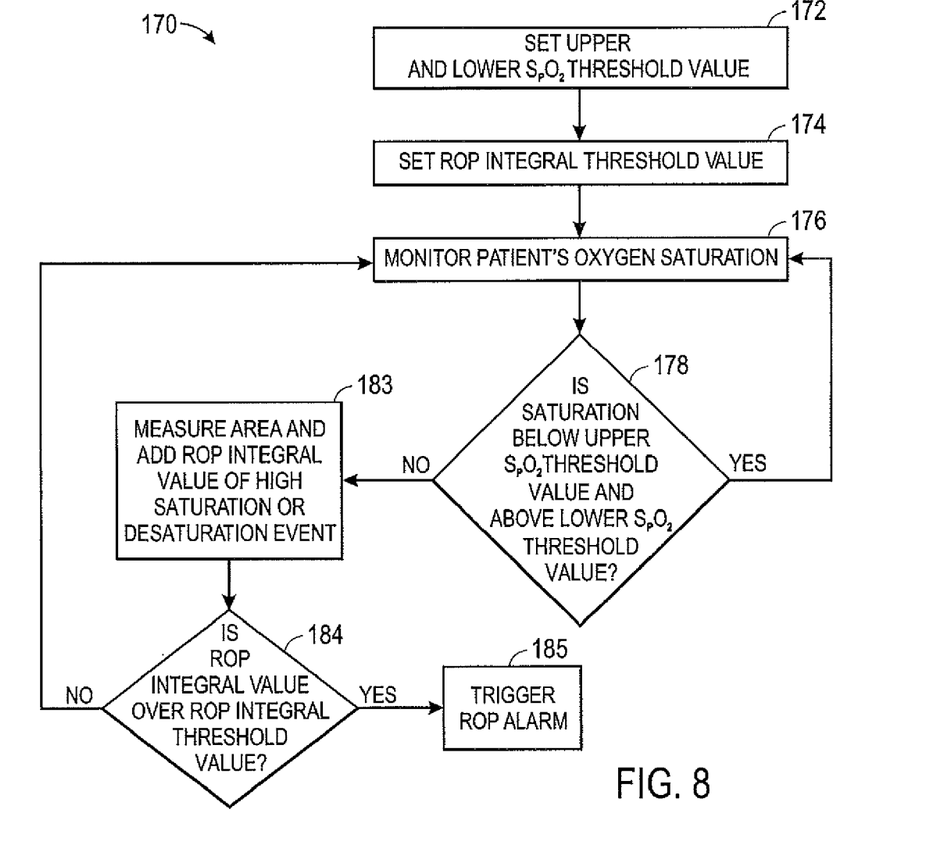
FIG. 8 is a further flow chart illustrating the operation of a retinopathy of prematurity alarm in accordance with the embodiment of FIG. 7.

The manner in which the ROP alarm system for both hyperoxemic and hypoxemic events as described with respect to FIG. 7 operates may be better understood with reference to the flow chart 170 presented in FIG. 8. As mentioned above, the monitor 10 may include an ROP module that may be activated to monitor the risk of developing ROP. Similar to methods 96 and 128 above, once activated, an upper $SpO_2$ threshold value and a lower $SpO_2$ threshold value for oxygen saturation may be set (block 172), as well as an ROP integral threshold value (block 174). In some embodiments, only a single $SpO_2$ threshold value may be set. The caregiver may set the upper $SpO_2$ threshold value, lower $SpO_2$ threshold value, and ROP integral threshold value. Alternatively, the caregiver may desire the monitor 10 to automatically set the upper threshold value and the lower threshold value, particularly in specific patient populations such as premature infants. As mentioned above, the monitor 10 may be able to select the appropriate threshold values based on specific patient features. The monitor 10 may monitor the patient's oxygen saturation (block 176), and the saturation level may be compared to the upper threshold value and the lower threshold value to determine if the saturation level is below the upper $SpO_2$ threshold value and above the lower $SpO_2$ threshold value (block 178). In embodiments with the single threshold value, the saturation level may be compared to the single threshold value to determine if the saturation level is above or below the threshold value. If the saturation level is between the lower and upper threshold values, then monitoring of the patient's oxygen saturation may continue (block 176).

If the saturation level is neither below the upper $SpO_2$ threshold value nor above the lower $SpO_2$ threshold value, i.e., a high saturation or desaturation event occurs where the saturation level deviates above the upper threshold value or below the lower threshold value, respectively, then an area or ROP integral value may be measured as a product of the duration of the high saturation or desaturation event and the amount or percentage points the saturation level deviates above the upper threshold value or below the lower threshold value and added to the total ROP integral value (block 183). For example, if the upper threshold value is set at 93 percent, then a saturation value of 98 percent would deviate from the upper threshold value by 5 points. These points may then be multiplied by the time or duration of an event (e.g., 2 minutes) to get an area or ROP integral value of 10. As mentioned above, the ROP integral threshold value, ranging up to 240 minutes, may be preset or entered by a caregiver. Upon the addition of the ROP integral value, a determination may be made as to whether the total ROP integral value is over the ROP integral threshold value (block 184). If the total ROP integral value does not exceed the ROP integral threshold value, the monitoring of the patient's oxygen saturation may continue (block 176).

If during the monitoring of a patient's oxygen saturation levels, the total ROP integral value meets the ROP integral threshold value an ROP alarm may be triggered (block 185). The ROP alarm may alert the caregiver that the patient 30, e.g., the premature infant, has suffered enough hyperoxemic events, hypoxemic events, or a combination thereof that pose a risk of developing ROP. The caregiver may want to be aware of such a risk to begin a therapy or treatment or to alter an existing therapy or treatment to the patient 30 to avoid an increased risk of developing ROP or to alleviate any damage that may have already occurred. The alarm may be as described above.

As briefly mentioned above, patient specific parameters may be incorporated into embodiments of the ROP alarm system. The ROP alarm system may incorporate patient specific parameters, among other factors, to set the threshold levels to better indicate when specific patients 30 may be at risk of developing ROP. Infants of low weight and early gestational age may be more at risk of developing ROP. Thus, being able to input patient specific parameters may be of interest to a caregiver to more closely monitor these high risk patients 30 and to tailor the ROP module and related thresholds to the infant and the infant's specific risk of developing ROP. Various algorithms and/or look-up tables may be employed by the monitor 10 to use these patient parameters to determine the threshold $SpO_2$ values and/or the ROP integral threshold value. The patient parameters may include body weight or gestational age, for example, and other parameters, such as body length, head circumference, or other factors may be used as well.

As mentioned above, an algorithm may be used to take these patient specific parameters and calculate the appropriate upper threshold level, lower threshold level, and/or ROP integral threshold value. For example, the patient parameters may be incorporated to determine the ROP integral threshold value (ROP ITV) using the following equation:

$$\text{Age}(W_1) + \text{Weight}(W_2) = \text{ROP ITV}$$

wherein $W_1$ is the weighted factor for gestational age and $W_2$ is the weighted factor for weight. The weighted factors, $W_1$ and $W_2$, may be different from each other. A gestational age of 40 weeks and a weight of 5 pounds may result in an ROP integral threshold value of 240 minutes, while a gestational age of 26 weeks and 1 pound may result in an ROP integral threshold value of 120 minutes. An infant at a gestational age of 40 weeks and a weight of 5 pounds may be given a larger ROP integral threshold value than an infant at a gestational age of 26 weeks and a weight of 1 pound may be given because the older and heavier baby may be at less of a risk of developing ROP.

Other patient parameters may be used to calculate the ROP integral threshold value as in the following equation:

$$\text{Age}(W_1) + \text{Weight}(W_2) + \text{Head Circumference}(W_3) + \text{Length}(W_4) = \text{ROP ITV}$$

wherein $W_1$, $W_2$, $W_3$, and $W_4$ are the weighted factors for gestational age, weight, head circumference, and length, respectively. The weighted factors $W_1$, $W_2$, $W_3$, and $W_4$ may be different from each other.

Alternatively, the patient parameters may be used to calculate a number that may be used in a look-up table to determine the appropriate upper threshold level, lower threshold level, and/or ROP integral threshold value, as in the following equation:

$$\text{Age}(W_1) + \text{Weight}(W_2) = L$$

wherein $W_1$ is the weighted factor for gestational age, $W_2$ is the weighted factor for weight, and L represents the look-up number. The weighted factors, $W_1$ and $W_2$, may be different from each other. The look-up number, L, may be found in a look-up table associated with a specific upper threshold level, lower threshold level, and/or ROP integral threshold value.

Alternative to algorithms, the threshold $SpO_2$ values and the ROP integral threshold value may be determined solely by a look-up table. The look-up table may have specific upper and/or lower threshold $SpO_2$ values, as well as an ROP integral threshold value, associated with a patient parameter (e.g., gestational age). For example, a gestational age of 26 weeks may be associated with a lower and upper threshold value of 88 and 92, respectively, and a ROP integral threshold value of 120. A gestational age of 36 weeks may be associated with a lower and upper threshold of 90 and 94, respectively, and a ROP integral threshold value of 180 since the infant may be at a lower risk of developing ROP due to an older gestational age. Premature neonatal patients have retinas that are not fully developed. The degree of development is usually proportional to the gestational age. The retinal growth and development is affected by oxygen levels in the arterial blood as well as perfusion changes in the blood vessels in the area of the retina. Thus, the more premature the neonate the greater the risk for developing ROP. The accumulative time a neonatal patient's $SpO_2$ is outside of the 88 percent to 92 percent range combined with greater degrees of prematurity will likely yield higher and more sever occurrences of ROP.

Figure 9:
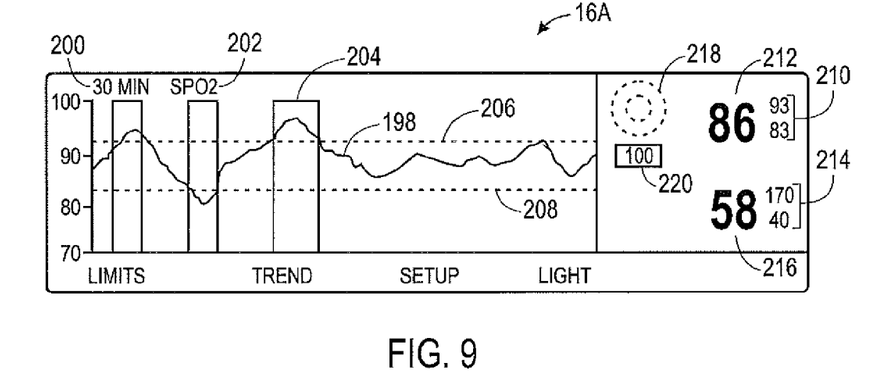
FIG. 9 is a representation of a display presenting features associated with a retinopathy of prematurity alarm system in accordance with the embodiment of FIG. 8.

Aspects of the above embodiments of the ROP alarm system may be visualized on the display 16 of the monitor 10. FIG. 9 illustrates an embodiment of such a display 16A using the ROP alarm embodied in FIG. 8. The display 16A may include trend data, alarm limits, or current settings for the monitor. The display 16A may also include a representative $SpO_2$ curve 198. The representative $SpO_2$ curve 198 may be a historical trend for a patient 30 monitored by the patient monitor 10. A label 200 may identify the length of the trend shown, in this case, 30 minutes. The display 16A also may include a label 202 indicating the type of physiological data shown by the representative $SpO_2$ curve 198, in this case, oxygen saturation.

Sections 204 of the representative $SpO_2$ curve 198 may be highlighted to identify excursions outside of the threshold limits indicated by dashed lines 206 and 208 on the display 16A. Lines 206 and 208 may represent the upper and lower threshold limits respectively for oxygen saturation. The display 16A may also include settings 210 for the oxygen saturation threshold limits, as well as an indicator 212 of the current oxygen saturation level. Besides oxygen saturation, the display 16A may include settings 214 for pulse rate, as well as an indicator 216 of the current pulse rate.

An ROP indicator 218 may also be shown on the display 16A. The ROP indicator 218 may have an annular dashed shape. The ROP indicator 218 may also be shaped like a square, triangle, rectangle, eye, or any other suitable shape. Deviations of the saturation level above the upper threshold (line 206) or below the lower threshold (line 208) may result in the calculation of an area, based on the integral of the difference between the saturation level and the threshold limit and time, which may be added to the total ROP integral value, as described above. The ROP indicator 218 may graphically fill in a clockwise direction as the total ROP integral value increases and/or may graphically decrease in a counterclockwise direction as the total ROP integral value decreases. For example, as shown, with a total ROP integral value of 0, the ROP indicator 218 may be empty. Besides the ROP indicator 218, the display 16A may include a label 220 that indicates the set ROP integral threshold value. As mentioned above, the ROP integral threshold value may range up to 240 minutes. For example, as shown, the label 220 indicates an ROP integral threshold value set at 100.

Figure 10:
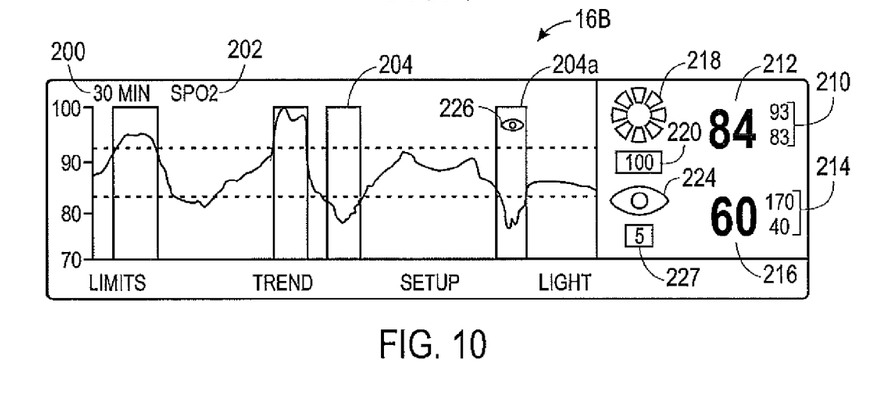
FIG. 10 is a representation of a display presenting features associated with a retinopathy of prematurity alarm system including a retinopathy of prematurity alarm in accordance with the embodiment of FIG. 8.

When the total ROP integral value reaches the ROP integral threshold value, indicator 218 is "full" and an alarm is given. The total ROP integral value (represented by the shaded area) may completely fill the ROP indicator 218, as shown in an embodiment of a display 16B illustrated in FIG. 10. The display 16B may include similar features to display 16A. The filled ROP indicator 218 may indicate the total ROP integral value at least meets the ROP integral threshold value of 100 as indicated by label 220. As described above, if the total ROP integral value meets the ROP integral threshold value, an ROP alarm may be triggered to indicate to the caregiver that the infant may be at risk of developing ROP. An audible alarm may be provided via the speaker 20 of the monitor 10 and/or a graphical element 224 may appear on the display 16B to indicate to the caregiver the ROP alarm. For example, the graphical element 224 may be represented by an eye shape since ROP affects a retina of the eye. In other embodiments, the graphical element 224 may have an alternative form or shape. The graphical element 224 may have the same color as the other features on the display or may have a different color (e.g., red) to set the graphical element apart from the other features and to get the attention of the caregiver. Further, the graphical element 224 may also flash to get the caregiver's attention. Also, a graphical element 226, similar to graphical element 224, may be displayed within one of the highlighted sections 204 of the representative $SpO_2$ curve to indicate when the ROP alarm is triggered. For example, the graphical element 226 may appear in highlighted section 204a that identifies a desaturation or hyperoxemic event that triggered the ROP alarm. Additionally, the degree of risk of developing ROP may be associated with a number as indicated by label 227. For example, the numbers may range from 1 to 5 with 1 representing a slight risk of developing ROP and 5 representing a severe risk of developing ROP. Determining the risk of developing ROP may include factors such as the percentage of time of hypoxemic and/or hyperoxemic events outside the threshold levels, the number of hypoxemic and/or hypoxemic events outside the threshold levels, and the slope of the time or percentage of time of hypoxemic and/or hyperoxemic events outside the threshold levels.

While some of the embodiments above describe an ROP module associated with a monitor 10, the ROP module and associated processing components may be incorporated into a multi-parameter monitor, cables, or some other electronic device to determine the risk of developing ROP and/or provide an alarm for such risk. The multi-parameter monitor, cables, or electronic device may be provided the oxygen saturation levels and/or patient parameters from the monitor 10 or another electronic device in real time to monitor for the risk of developing ROP. Alternatively, historical data that includes oxygen saturation levels and/or patient parameters may be downloaded or acquired from the monitor 10 or another source. The ROP module incorporated with the monitor 10 may also determine the risk of developing ROP from historical data.

In response to an ROP alarm, the caregiver may perform an eye exam on the infant to determine if any abnormal blood vessel development is occurring in the infant. ROP consists of five stages ranging from mildly abnormal blood vessel growth (stage 1) to total retinal detachment (stage 5). If abnormal blood vessel development is occurring, then the caregiver may utilize a variety of treatments or therapies at their disposal to alleviate any potential damage to the infant's vision. These treatments or therapies, in some cases, may be used as a preventative to avoid the development of ROP. For example, laser ablation therapy may be used to stop the growth of abnormal blood vessels. Also, cryotherapy may also be used to stop the growth of abnormal vessels. In addition, drug therapies, such as vitamin E supplementation, may be utilized to alleviate the severity of ROP. Alternatively, oxygen therapy may be used to hinder the progression of ROP.

Figure 11:
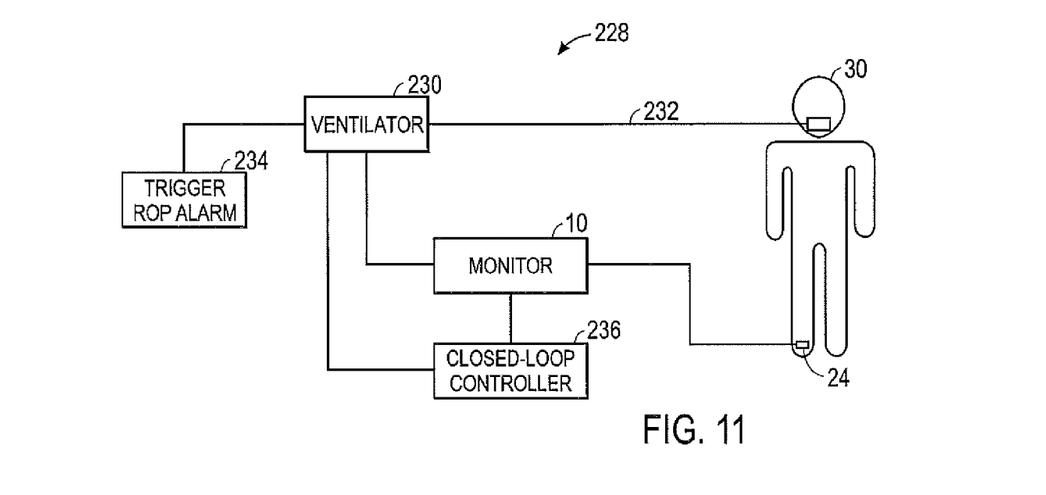
FIG. 11 is a block diagram of a closed-loop ventilation system to manage oxygen saturation levels in accordance with another embodiment.

Alternatively, the effects of hyperoxemic and hypoxemic events on the development of ROP may be reduced by regulating the amount of oxygen received by an infant while monitoring the infant with a monitor 10 that employs the ROP module described above. FIG. 11 illustrates the use of a closed-loop ventilation system 228 to manage oxygen saturation levels. The ventilation system 228 may include a ventilator 230 to administer a controlled gas mixture to the patient via an inspiration line 232 applied to patient 30. The ventilator may be coupled to a gas mixture supply 234 which may provide the gas mixture for the inspiration line 232. The gas mixture supply 234 may include a mixture of air, oxygen, and/or nitrogen, for example. The ventilator 230 may include an input for the user to enter the amount of oxygen to be delivered to the patient 30. The constituents of the gas mixture delivered in the inspiration line 232 may be altered by the ventilator 230 in response to signals received from the monitor 10 and/or a closed-loop controller 236. The monitor 10 may include a pulse oximeter, as described above. The monitor 10 may calculate oxygen saturation levels, among other physiological parameters, via signals received from the sensor 24 coupled to the patient 30. In addition, the monitor 10 may employ and manage an ROP module, as described above.

The closed-loop controller 236 may be coupled to the monitor 10. In some embodiments, the closed-loop controller may be integrated into the monitor 10. The closed-loop controller 236 may include a set oxygen saturation point or set oxygen saturation range for the patient 30. The set oxygen saturation point or range may be provided to the closed-loop controller 236 by the monitor 10. The oxygen saturation point or range may be determined by the ROP threshold limits employed by the ROP module within the monitor 10. The monitor 10 also may provide to the closed-loop controller 236 the current oxygen saturation level of the patient 30. In response to receiving the current oxygen saturation level, the closed-loop controller 230 may send a signal to the ventilator to administer a specific gas mixture via the inspiration line 232 to the patient 30 in order to bring or to maintain the patient's oxygen saturation level at the set oxygen saturation point or within the set oxygen saturation range. For example, a patient 30 may have a current oxygen saturation level of 95 percent. The upper and lower ROP threshold limits may be set at 88 percent and 92 percent, respectively. The closed-loop controller 236 may send a signal to the ventilator 230 to administer a gas mixture to the patient 30 to bring the oxygen saturation level within the upper threshold limit of 92 percent. Alternatively, the current oxygen saturation level of the patient 30 may be at 91 percent but trending upward. In this scenario, the closed-loop controller 234 may send a signal to the ventilator 230 to administer a gas mixture to the patient 30 to maintain the oxygen saturation level within the threshold limits.

The closed-loop controller 236 may include a memory storing an algorithm configured to calculate adjustments for inducing, maintaining, and/or controlling physiological parameters of the patient 30. Such algorithms (e.g., P, PD, PT, and PID algorithms) may be utilized to bring the patient's physiological parameters to a desired state. For example, predefined proportional, integral, and/or derivative factors may be designated to facilitate tuning control loops based on physical characteristics of the patient (e.g., gestational age or weight). In a specific example, certain integral factors for designated patient types may be used in a PI controller algorithm to make sure a certain patient $SpO_2$ level is approached steadily. Additionally, other loop tuning factors (e.g., a derivative factor) may be utilized to improve control.

Figure 12:
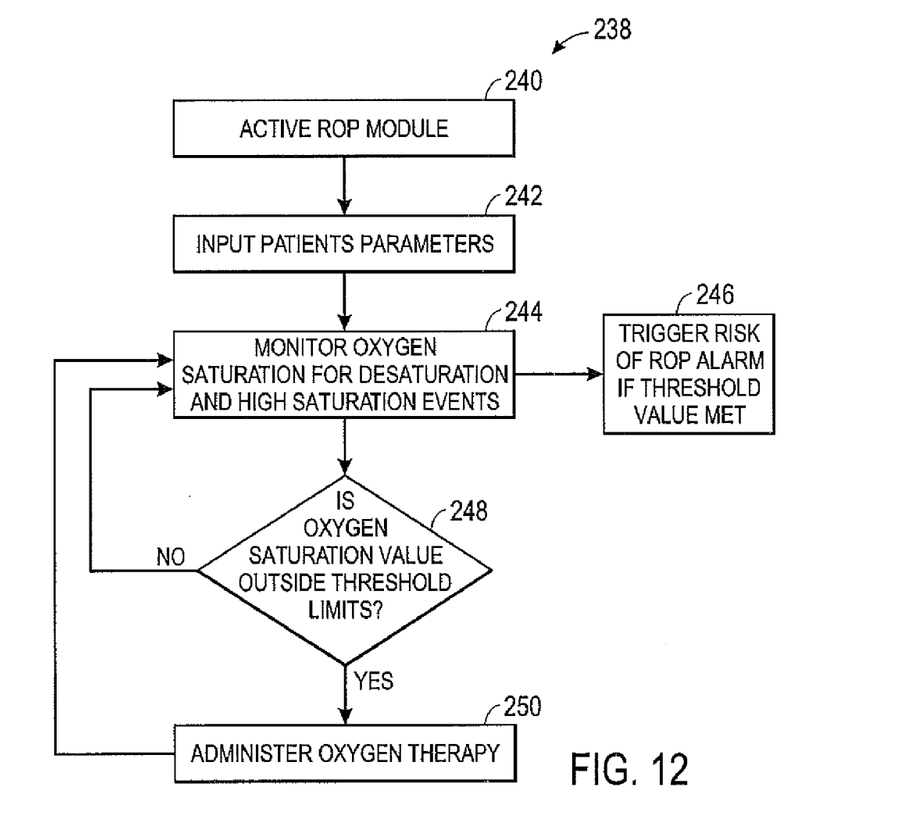
FIG. 12 is a flow chart illustrating the employment of a retinopathy of prematurity module in conjunction with a closed-loop administration of oxygen therapy in accordance with the embodiment of FIG. 11.

As discussed above, oxygen therapy may be administered to avoid or mitigate the effects of ROP. FIG. 12 illustrates a method 238 employing an ROP module in conjunction with a closed-loop administration of oxygen therapy using the closed-loop ventilation system 228 embodied in FIG. 11. The method 238 may begin similar to method 186 above with the activation of an ROP module (block 240). The present embodiment may activate an ROP module that monitors both hyperoxemic and hypoxemic events, as described above. In other embodiments, the activated ROP module may solely monitor hyperoxemic events or solely monitor hypoxemic events, as described above. Following activation of the ROP module, patient parameters may be input (block 242) into the monitor 10. Patient parameters (e.g., gestational age) may be input as described above. As mentioned above, an algorithm may be used to take these patient specific parameters and calculate the appropriate upper threshold level, lower threshold level, and/or ROP integral threshold value. These threshold levels may also be used to determine an oxygen saturation range to be used by the monitor 10 and/or closed-loop controller 236 in which to maintain the patient's oxygen saturation level. A set oxygen saturation point may also be determined from the threshold levels. For example, if upper and lower threshold levels are both used, then the set oxygen saturation point may be the average of the threshold levels. For example, oxygen threshold levels of 92 percent and 88 percent may yield a set oxygen saturation point of 90 percent.

Once the threshold levels are set, the ROP module may monitor oxygen saturation levels for desaturation and high saturation events (block 244). As described above, the addition of integrated areas of the saturation level above an upper threshold level and/or below a lower threshold level, along with reductions due to normal oxygen saturation levels, may be used to determine a total ROP integral value. If this total ROP integral value meets the ROP integral threshold value, the ROP alarm may be triggered (block 246). However, simultaneously, the monitor 10 may continuously make a determination whether the oxygen saturation value of the patient 30 is outside the threshold limits (block 248). If the oxygen saturation value does not fall outside the threshold limits, then the ROP module may continue to monitor oxygen saturation levels for desaturation and high saturation events (block 244). If the oxygen saturation value does fall outside threshold limits, oxygen therapy may be administered (block 250). The administration of the oxygen therapy may be under the control of closed-loop controller 236 and administered via ventilator 230, described above. The administered oxygen therapy may be used to return the oxygen saturation level of the patient 30 to within the threshold limits without the need of a caregiver's presence. In another embodiment, the closed-loop administration of oxygen therapy may be used to maintain the oxygen saturation level of the patient 30 within the threshold limits. The closed-loop administration of oxygen therapy may reduce the odds of triggering the ROP alarm and may reduce the chances of an infant developing ROP due to hyperoxemic and hypoxemic events.

The above embodiments describe the ROP module measuring the integral of hyperoxemic and/or hypoxemic events outside of the threshold levels in monitoring for the risk of developing ROP. In other embodiments, the ROP module may measure the time of hyperoxemic and/or hypoxemic events outside of the threshold levels and use a total ROP threshold level that has a value defined only by time (e.g., 120 minutes) outside of the threshold levels. In some embodiments, the ROP module may measure the percentage of time of hyperoxemic and/or hypoxemic events outside of the threshold levels. In further embodiments, the ROP module may also monitor the number of hyperoxemic and/or hypoxemic events outside of the threshold levels.

Further, the above embodiments describe the use of the ROP module in conjunction with a device (e.g., pulse oximeter) to measure $SpO_2$ levels. Those of ordinary skill in the art would appreciate that the ROP module may be incorporated with other devices to monitor other related measures of blood oxygen for the risk of developing ROP, such as transcutaneous oxygen tension ($TeO_2$), partial pressure of oxygen in arterial blood ($PaO_2$), and other measures.

What is claimed is:

1. An apparatus for determining a risk of retinopathy of prematurity in a patient, the apparatus comprising:
   a processing unit configured to:
   determine whether an oxygen saturation level of the patient extends beyond an oxygen saturation threshold;
   determine an extent that the oxygen saturation level of the patient extends beyond the oxygen saturation threshold; and
   trigger an alarm when the extent that the oxygen saturation level of the patient extends beyond the oxygen saturation threshold exceeds a threshold at which the patient may be at risk of developing retinopathy of prematurity; and
   a display unit configured to present the alarm in response to the trigger from the processing unit.

2. The apparatus of claim 1, wherein the processing unit is configured to measure the oxygen saturation level of the patient.

3. The apparatus of claim 1, wherein the processing unit is configured to receive the oxygen saturation level from another device.

4. The apparatus of claim 1, wherein the oxygen saturation level comprises historical data.

5. The apparatus of claim 1, wherein the oxygen saturation threshold corresponds to a hyperoxemic oxygen saturation value, a hypoxemic oxygen saturation value, or both.

6. The apparatus of claim 1, wherein the oxygen saturation threshold is automatically set based on one or more patient parameters, which comprise one or more of gestational age, weight, length, and head circumference.

7. The apparatus of claim 1, wherein the extent comprises an integral of excursion of oxygen saturation level beyond oxygen saturation threshold.

8. The apparatus of claim 1, wherein the extent comprises a product of an amount of excursion and time of excursion beyond oxygen saturation threshold.

9. The apparatus of claim 1, wherein the threshold is automatically set based on one or more patient parameters, which comprise one or more of gestational age, weight, length, and head circumference.

10. The apparatus of claim 1, wherein the display comprises a number associated with the risk of developing retinopathy of prematurity.

11. A method for determining a risk of retinopathy of prematurity in a patient, the method comprising:
    determining whether an oxygen saturation level of the patient extends beyond an oxygen saturation threshold;
    determining an extent that the oxygen saturation level of the patient extends beyond the oxygen saturation threshold; and
    presenting an alarm when the extent that the oxygen saturation level of the patient extends beyond the oxygen saturation threshold exceeds a threshold at which the patient may be at risk of developing retinopathy of prematurity.

12. The method of claim 11, comprising measuring the oxygen saturation level of the patient.

13. The method of claim 11, wherein the oxygen saturation threshold corresponds to a hyperoxemic oxygen saturation value, hypoxemic oxygen saturation value, or both.

14. The method of claim 11, comprising automatically setting the oxygen saturation threshold based on one or more patient parameters, which comprise one or more of gestational age, weight, length, and head circumference.

15. The method of claim 11, wherein the extent comprises an integral of excursion of oxygen saturation level beyond oxygen saturation threshold.

16. The method of claim 11, wherein the extent comprises a product of an amount of excursion and time of excursion beyond oxygen saturation threshold.

17. The method of claim 11, comprising automatically setting the threshold based on one or more patient parameters, which comprise one or more of gestational age, weight, length, and head circumference.

18. The method of claim 11, comprising presenting a number associated with the risk of developing retinopathy of prematurity.

19. A pulse oximeter, comprising:
    a sensor configured to generate a physiological signal; and
    a processing unit configured to:
    measure the oxygen saturation level of the patient based on data derived from the physiological signal;
    determine whether an oxygen saturation level of the patient extends beyond an oxygen saturation threshold;
    determine an extent that the oxygen saturation level of the patient extends beyond the oxygen saturation threshold; and
    trigger an alarm when the extent that the oxygen saturation level of the patient extends beyond the oxygen saturation threshold exceeds a threshold at which the patient may be at risk of developing retinopathy of prematurity.

20. The pulse oximeter of claim 19, comprising a display unit configured to present the alarm in response to the trigger from the processing unit.

* * * * *